US005973133A

United States Patent [19]
Hardy et al.

[11] Patent Number: 5,973,133
[45] Date of Patent: Oct. 26, 1999

[54] MUTANT S182 GENES

[75] Inventors: John A. Hardy, St. Augustine, Fla.; Alison M. Goate, Richmond Heights, Mo.

[73] Assignees: Washington University, St. Louis, Mo.; University of South Flordia, Tampa, Fla.

[21] Appl. No.: 08/670,479

[22] Filed: Jun. 26, 1996

Related U.S. Application Data

[60] Provisional application No. 60/001,500, Jul. 18, 1995, and provisional application No. 60/001,800, Aug. 2, 1995.

[51] Int. Cl.$^6$ .................................................. C07H 21/04
[52] U.S. Cl. ..................... 536/23.5; 536/23.1; 530/350; 514/2; 514/44; 800/12; 435/4; 435/6
[58] Field of Search ............................... 800/2, DIG. 1–4, 800/12; 530/350; 536/23.1, 23.5; 435/6, 172.3, 4; 514/44, 2

[56] References Cited

U.S. PATENT DOCUMENTS

| | | | |
|---|---|---|---|
| 5,387,742 | 2/1995 | Cordell | 800/2 |
| 5,545,808 | 8/1996 | Hew et al. | 800/2 |

OTHER PUBLICATIONS

Pursel et al. Genetic Engineering of Livestock. Science, vol. 244, pp. 1281–1288, Jun. 16, 1989.

Houdebine, L. M. Production of pharmaceutical proteins from transgenic animals. J. of Biotech., vol. 34, pp. 269–287, 1994.

Salter, et al. Transgenic chickens: insertion of retroviral genes into the chicken germ line. Virology, vol. 157, pp. 236–240, 1987.

Sherrington et al. Cloning of gene bearing missense mutations in early–onset familial Alzheimer's disease. Nature, vol. 375, pp. 754–760, Jun. 29, 1995.

Wragg et al. Animal models of Alzheimer's disease. Adaptations in Aging, Academic Press, pp. 157–172, 1995.

Price et al. Biology of Alzheimer's disease and animal models. The American Psychiatric Press textbook of Psychopharmacology, American Psychiatric Press, Inc, pp. 523–535, 1995.

*Primary Examiner*—Brian R. Stanton
*Assistant Examiner*—Deborah J. R. Clark
*Attorney, Agent, or Firm*—Ratner & Prestia; William T. King; Elizabeth J. Hecht

[57] ABSTRACT

The invention provides novel mutant S182 sequences, methods of diagnosing Alzheimer's disease using these novel mutant S182 genes, a model system for Alzheimer's disease comprising a mutant S182 gene, and methods of identifying mutations in genes homologous to the S182 gene.

33 Claims, 4 Drawing Sheets

FIGURE 1A

```
          11           20           29           38           47           56
5' CCG TAC GTA GCC GCG GCG GCA GCG GGG CGG CGG GGA AGC GTA TGC ATA CAA ATT
   --- --- --- --- --- --- --- --- --- --- --- --- --- --- --- --- --- ---

65           74           83           92          101          110
   TAT TAG CAT GCA GAC TGG GAG AAC CAC AAG ACC TAA TCT GGG AGC CTG CAA GTG
   --- --- --- --- --- --- --- --- --- --- --- --- --- --- --- --- --- ---

119          128          137          146          155          164
   ACA ACA GCC TTT GCG GTC CTT AGA CAG CTT GGC CTG GAG GAG AAC ACA TGA AAG
   --- --- --- --- --- --- --- --- --- --- --- --- --- --- --- --- --- ---

173          182          191          200          209          218
   AAA GAA CCT CAA GAG GCT TTG TTT TCT GTG AAA CAG TAT TTC TAT ACA GTT GCT
   --- --- --- --- --- --- --- --- --- --- --- --- --- --- --- --- --- ---

227          236          245          254          263          272
   CCA ATG ACA GAG TTA CCT GCA CCG TTG TCC TAC TTC CAG AAT GCA CAG ATG TCT
   --- --- --- --- --- --- --- --- --- --- --- --- --- --- --- --- --- ---
        M   T   E   L   P   A   P   L   S   Y   F   Q   N   A   Q   M   S 281          290          299          308          317          326
   GAG GAC AAC CAC CTG AGC AAT ACT AAT GAC AAT AGA GAA CGG CAG GAG CAC AAC
   --- --- --- --- --- --- --- --- --- --- --- --- --- --- --- --- --- ---
    E   D   N   H   L   S   N   T   N   D   N   R   E   R   Q   E   H   N 335          344          353          362          371          380
   GAC AGA CGG AGC CTT GGC CAC CCT GAG CCA TTA TCT AAT GGA CGA CCC CAG GGT
   --- --- --- --- --- --- --- --- --- --- --- --- --- --- --- --- --- ---
    D   R   R   S   L   G   H   P   E   P   L   S   N   G   R   P   Q   G 389          398          407          416          425          434
   AAC TCC CGG CAG GTG GTG GAG CAA GAT GAG GAA GAA GAT GAG GAG CTG ACA TTG
   --- --- --- --- --- --- --- --- --- --- --- --- --- --- --- --- --- ---
    N   S   R   Q   V   V   E   Q   D   E   E   E   D   E   E   L   T   L 443          452          461          470          479          488
   AAA TAT GGC GCC AAG CAT GTG ATC ATG CTC TTT GTC CCT GTG ACT CTC TGC ATG
   --- --- --- --- --- --- --- --- --- --- --- --- --- --- --- --- --- ---
    K   Y   G   A   K   H   V   I   M   L   F   V   P   V   T   L   C   M 497          506          515          524          533          542
   GTG GTG GTC GTG GCT ACC ATT AAG TCA GTC AGC TTT TAT ACC CGG AAG GAT GGG
   --- --- --- --- --- --- --- --- --- --- --- --- --- --- --- --- --- ---
    V   V   V   V   A   T   I   K   S   V   S   F   Y   T   R   K   D   G
```

FIGURE 1B

```
      551             560             569             578             587             596
CAG CTA ATC TAT ACC CCA TTC ACA GAA GAT ACC GAG ACT GTG GGC CAG AGA GCC
--- --- --- --- --- --- --- --- --- --- --- --- --- --- --- --- --- ---
 Q   L   I   Y   T   P   F   T   E   D   T   E   T   V   G   Q   R   A 605             614             623             632             641             650
CTG CAC TCA ATT CTG AAT GCT GCC ATC ATG ATC AGT GTC ATT GTT GTC ATG ACT
--- --- --- --- --- --- --- --- --- --- --- --- --- --- --- --- --- ---
 L   H   S   I   L   N   A   A   I   M   I   S   V   I   V   V   M   T 659             668             677             686             695             704
ATC CTC CTG GTG GTT CTG TAT AAA TAC AGG TGC TAT AAG GTC ATC CAT GCC TGG
--- --- --- --- --- --- --- --- --- --- --- --- --- --- --- --- --- ---
 I   L   L   V   V   L   Y   K   Y   R   C   Y   K   V   I   H   A   W 713             722             731             740             749             758
CTT ATT ATA TCA TCT CTA TTG TTG CTG TTC TTT TTT TCA TTC ATT TAC TTG GGG
--- --- --- --- --- --- --- --- --- --- --- --- --- --- --- --- --- ---
 L   I   I   S   S   L   L   L   L   F   F   F   S   F   I   Y   L   G 767             776             785             794             803             812
GAA GTG TTT AAA ACC TAT AAC GTT GCT GTG GAC TAC ATT ACT GTT GCA CTC CTG
--- --- --- --- --- --- --- --- --- --- --- --- --- --- --- --- --- ---
 E   V   F   K   T   Y   N   V   A   V   D   Y   I   T   V   A   L   L 821             830             839             848             857             866
ATC TGG AAT TTT GGT GTG GTG GGA ATG ATT TCC ATT CAC TGG AAA GGT CCA CTT
--- --- --- --- --- --- --- --- --- --- --- --- --- --- --- --- --- ---
 I   W   N   F   G   V   V   G   M   I   S   I   H   W   K   G   P   L 875             884             893             902             911             920
CGA CTC CAG CAG GCA TAT CTC ATT ATG ATT AGT GCC CTC ATG GCC CTG GTG TTT
--- --- --- --- --- --- --- --- --- --- --- --- --- --- --- --- --- ---
 R   L   Q   Q   A   Y   L   I   M   I   S   A   L   M   A   L   V   F 929             938             947             956             965             974
ATC AAG TAC CTC CCT GAA TGG ACT GCG TGG CTC ATC TTG GCT GTG ATT TCA GTA
--- --- --- --- --- --- --- --- --- --- --- --- --- --- --- --- --- ---
 I   K   Y   L   P   E   W   T   A   W   L   I   L   A   V   I   S   V 983             992            1001            1010            1019            1028
TAT GAT TTA GTG GCT GTT TTG TGT CCG AAA GGT CCA CTT CGT ATG CTG GTT GAA
--- --- --- --- --- --- --- --- --- --- --- --- --- --- --- --- --- ---
 Y   D   L   V   A   V   L   C   P   K   G   P   L   R   M   L   V   E 1037            1046            1055            1064            1073            1082
ACA GCT CAG GAG AGA GAT GAA ACG CTT TTT CCA GCT CTC ATT TAC TCC TCA ACA
--- --- --- --- --- --- --- --- --- --- --- --- --- --- --- --- --- ---
 T   A   Q   E   R   D   E   T   L   F   P   A   L   I   Y   S   S   T 1091            1100            1109            1118            1127            1136
ATG GTG TGG TTG GTG AAT ATG GCA GAA GGA GAC CCG GAA GCT CAA AGG AGA GTA
```

FIGURE 1C

```
            M   V   W   L   V   N   M   A   E   G   D   P   E   A   Q   R   R   V
           1145        1154        1163        1172        1181        1190
        TCC AAA AAT TCC AAG TAT AAT GCA GAA AGC ACA GAA AGG GAG TCA CAA GAC ACT
         S   K   N   S   K   Y   N   A   E   S   T   E   R   E   S   Q   D   T
           1199        1208        1217        1226        1235        1244
        GTT GCA GAG AAT GAT GAT GGC GGG TTC AGT GAG GAA TGG GAA GCC CAG AGG GAC
         V   A   E   N   D   D   G   G   F   S   E   E   W   E   A   Q   R   D
           1253        1262        1271        1280        1289        1298
        AGT CAT CTA GGG CCT CAT CGC TCT ACA CCT GAG TCA CGA GCT GCT GTC CAG GAA
         S   H   L   G   P   H   R   S   T   P   E   S   R   A   A   V   Q   E
           1307        1316        1325        1334        1343        1352
        CTT TCC AGC AGT ATC CTC GCT GGT GAA GAC CCA GAG GAA AGG GGA GTA AAA CTT
         L   S   S   S   I   L   A   G   E   D   P   E   E   R   G   V   K   L
           1361        1370        1379        1388        1397        1406
        GGA TTG GGA GAT TTC ATT TTC TAC AGT GTT CTG GTT GGT AAA GCC TCA GCA ACA
         G   L   G   D   F   I   F   Y   S   V   L   V   G   K   A   S   A   T
           1415        1424        1433        1442        1451        1460
        GCC AGT GGA GAC TGG AAC ACA ACC ATA GCC TGT TTC GTA GCC ATA TTA ATT GGT
         A   S   G   D   W   N   T   T   I   A   C   F   V   A   I   L   I   G
           1469        1478        1487        1496        1505        1514
        TTG TGC CTT ACA TTA TTA CTC CTT GCC ATT TTC AAG AAA GCA TTG CCA GCT CTT
         L   C   L   T   L   L   L   L   A   I   F   K   K   A   L   P   A   L
           1523        1532        1541        1550        1559        1568
        CCA ATC TCC ATC ACC TTT GGG CTT GTT TTC TAC TTT GCC ACA GAT TAT CTT GTA
         P   I   S   I   T   F   G   L   V   F   Y   F   A   T   D   Y   L   V
           1577        1586        1595        1604        1613        1622
        CAG CCT TTT ATG GAC CAA TTA GCA TTC CAT CAA TTT TAT ATC TAG CAT ATT TGC
         Q   P   F   M   D   Q   L   A   F   H   Q   F   Y   I   *
           1631        1640        1649        1658        1667        1676
        GGT TAG AAT CCC ATG GAT GTT TCT TCT TTG ACT ATA ACA AAA TCT GGG GAG GAC
```

FIGURE 1D

```
      1685          1694         1703         1712         1721          1730
AAA GGT GRT TTT CCT GTG TCC CAC ATC TAA CAA AGT CAA GAT TCC CGK CTG GAC
--- --- --- --- --- --- --- --- --- --- --- --- --- --- --- --- --- ---

1739         1748         1757         1766         1775          1784
TTT TGC AGC TTC CTK CCA AGT CTT CCT GAC CAC CTT GCA CTW TTG GAC TTT GGA
--- --- --- --- --- --- --- --- --- --- --- --- --- --- --- --- --- ---

1793         1802         1811         1820         1829          1838
RGG AGG TGC CTA KAG AAA ACG RTT TTG AMC ATA CTT CAT CGC AGT GGA CTG TGT
--- --- --- --- --- --- --- --- --- --- --- --- --- --- --- --- --- ---

1847         1856         1865         1874         1883          1892
CCC TCG GTG CAG AAA CTA CCA GAT TTG AGG GAC GAG GTC AAG GAG ATA TGA TAG
--- --- --- --- --- --- --- --- --- --- --- --- --- --- --- --- --- ---

1901         1910
GCC CGG AAG TTG CTG TGC CCA TCA 3'
--- --- --- --- --- --- --- ---
```

MUTANT S182 GENES

This application claims the benefit of U.S. Provisional application Ser. No. 60/001,500, filed Jul. 18, 1995 and Provisional application Ser. No. 60/001,800 filed Aug. 2, 1995.

BACKGROUND OF THE INVENTION

Alzheimer's disease (AD) is a progressive degenerative disease of the central nervous system characterized clinically by dementia and neuropathologically by the presence of numerous senile plaques and neurofibrillary tangles. AD is typically a disease of the elderly, afflicting up to 6% of those aged 65 years and up to 20% of 80 years olds. This is termed late onset AD. In addition, a small number of pedigrees have been described wherein the disease is inherited as an autosomal dominant with age dependent penetrance. Most commonly, the age of onset of the disease is below 60 years in these families. This is termed early onset AD. Genetic factors have been implicated in both early and late onset AD.

At least three different genetic loci that confer inherited susceptibility to this disease have been identified.

The $\epsilon4$ (112CysArg) allele of the apolipoprotein E (ApoE) gene located on chromosome 19 is associated with AD in a significant proportion of cases with late onset. Strittmatter et al., *Proc. Nat'l. Acad. Sci.* USA 1993, 90:1977–1981; Saunders et al., *Neurology* 1993, 43:1467–1472. Inheritance of this allele has also been reported to lower the age of onset in a dose dependent manner. Corder et al., *Science* 1993, 261:921–923. Conversely, inheritance of the apolipoprotein E $\epsilon2$ allele appears to confer a decreased risk of developing AD. Corder et al., *Nature Genet.* 1994, 7:180–184. While the biochemical mechanism of these effects is still unclear, there are significantly increased numbers of A$\beta$ deposits in the brains of patients having one or two $\epsilon4$ alleles. Schmechel et al., *Proc. Nat'l. Acad. Sci.* USA 1993, 90:9649–9653; Hyman et al., *Proc. Nat'l. Acad. Sci.* USA 1995, 92:3586–3590.

Mutations in the gene for the $\beta$-amyloid precursor protein ($\beta$APP) on chromosome 21 have been found in a small number of families with disease onset before 65 years of age. Goate et al., *Nature* 1991, 349:704–706; Chartier-Harlin et al., *Nature* 1991, 353:844–846; Murrell et al., *Science* 1991, 254:97–99; Karlinsky et al., *Neurology* 1992, 42:1445–1453. These disease-causing mutations have been modelled in transfected or primary cultured cells and shown to lead to altered proteolytic processing of $\beta$APP in a way that favors production of its amyloidogenic and potentially neurotoxic A$\beta$ fragment. Further, transgenic overexpression of one mutant $\beta$APP has resulted in the first mouse model of AD, in which age-linked cerebral deposition of A$\beta$ is accompanied by neuronal, astrocytic and microglial pathology. Games et al., *Nature* 1995, 373:523–527.

A third locus (AD3) has been mapped by genetic linkage studies to chromosome 14q24.3 which may account for up to 70% of early-onset autosomal dominant AD. Schellenberg et al., *Science* 1992, 258:668–670; St. George-Hyslop et al., *Natur Genet.* 1992, 2:330–334; Van Broeckhoven et al., *Natur Genet.* 1992, 2:335–339. The AD3 locus is associated with the most aggressive form of this disease (onset 30 to 60 years of age) and it has been suggested that mutations at this locus put into effect a biologically fundamental process leading to AD. Sherrington et al., *Nature* 1995, 375:754–760.

A novel gene with five missense mutations in seven pedigrees segregating early-onset, autosomal dominant AD at the AD3 locus was recently cloned. Sherrington et al., *Nature* 1995, 375:754–760. This gene has been called S182. Analysis of the nucleotide sequences of the S182 transcript revealed heterozygous nucleotide substitutions in the reverse transcriptase-polymerase chain reaction products from affected members of six large pedigrees. Each of the nucleotide substitutions occurred within a putative open reading frame of the S182 transcript and are predicted to change the encoded amino acid at the following positions (numbering FAD4 and Torl.l; HisArg codon 163 in pedigree 603; AlaGlu at codon 246 in pedigree FAD1; LeuVal at codon 286 in pedigree FAD2; and CysTyr at codon 410 in pedigrees FAD3 and NIH2. of all the nucleotide substitution cosegregated with the disease in their respective pedigrees, none were seen in asymptomatic family members aged more than 2 standard deviations beyond the mean onset, and none were present on 284 chromosomes from unrelated neurologically normal subjects drawn from comparable ethnic origins. Sherrington et al., *Nature* 1995, 375:754–760.

A number of other mutant S182 genes have now been identified. These mutants are useful in the diagnosis of early-onset AD and in evaluating agents which may be useful for the treatment of this disease.

SUMMARY OF THE INVENTION

An object of the present invention is to provide novel mutant S182 sequences.

Another object of the present invention is to provide a method of diagnosing Alzheimer's disease using these novel mutant S182 genes.

Yet another object of the present invention is to provide a model system for Alzheimer's disease comprising a mutant S182 gene.

Yet another object of the present invention is to provide a method of identifying mutations in genes homologous to the S182 gene.

BRIEF DESCRIPTIONS OF THE FIGURES

FIGS. 1 A–D provides the nucleotide sequence and the encoded amino acid sequence of an S182 gene (SEQ. ID NOS:18 and 24).

DETAILED DESCRIPTION OF THE INVENTION

Genetic linkage strategies placed a gene causing early onset familial Alzheimer's disease (FAD) on the long arm of chromosome 14 between D14S289 and D14S61. Five mutations within the S182 gene, which map to this region, were recently reported in several families multiply affected by early onset AD. Sherrington et al., *Nature* 1995, 375:754–760.

A full length cDNA clone for S182 from a human brain library has now been isolated. Analysis of the sequence of this clone revealed that it is identical in predicted amino acid sequence to that predicted by Sherrington et al. with the exception of the absence of amino acids VRSQ at position 26–29. The nucleotide sequence and amino acid sequence of this clone is provided in FIG. 1. This gene has now been localized at a 100 kb region between previously identified markers, D14S77 and D14S668E. The intron-exon structure of this gene has now been determined along with evidence for alternative splicing of the S182 gene.

While the specification complies with the requirements of 35 USC §112 without a deposit of any biological material, solely for the convenience and benefit of the public, a full length cDNA clone of S182 from a human brain library was deposited with ATCC as Deposit Number 97238 (pcDNA+ S182 clone 1b) on Jul. 28, 1995 in compliance with Budapest Treaty. This clone will be made available irrevocably and without restriction, expect as conditioned by CFR 1.808(b), upon issuance of a patent. The depository address is the American Type Culture Collection, 12301 Parklawn Drive, Rockville, Md. 20852, USA.

In addition, a number of novel mutants in this S182 gene have now been identified in families multiply affected by early onset AD. Nucleotide substitutions were identified in the S182 transcript which are predicted to change the encoded amino acid at the following positions (numbering from the first putative initiation codon) MetVal at codon 135 in pedigrees F148 and F206; and MetVal at codon 142 in pedigrees Fin1, NY5201 and MAN92/20; ProSer at codon 263 in pedigree F196; GluAla at codon 276 in pedigrees C1, C2, C3 and 771; and GluGly at codon 276 in pedigree F183. In each case, the mutations have been identified only in afflicted members of each family. These mutations do not coincide with any of those described by Sherrington et al., *Nature* 1995, 375:754–760.

Forty families multiply affected by early onset AD were screened for mutations. Of these families only one family, which was believed to be a branch of FAD4, had a published mutation. However, several of these families demonstrated digest changes.

The family Fin1, described by Haltia et al., *Annals of Neurol.* 1994, 36:362–367, showed a change in the restriction pattern generated by the enzyme Rcal with primers 910/911. Primers 910: 5'-TCACAGAAGATACCGAGACT-3' (SEQ ID NO:1) and 911: 5'-CCCAACCATAAGAAGAACAG-3' (SEQ ID NO:2) are disclosed by Sherrington et al. in Nature 1995, 375:754–760. Direct sequencing of affected members of samples from this family revealed a mutation (AG) which occurs at the same nucleotide as the FAD4 mutation, but results in a different amino acid substitution, methionine to valine at codon 142 (referred to as codon 146 by Sherrington et al.) This mutation segregates with the disease. The same mutation was present in two other families, namely NY5201 and MAN92/20.

A sample from F148 (Mullan et al., *Nature Genet.* 1992, 2:340–343) also showed a change in digest pattern with the same enzyme and primers. However, this pattern was different. Direct sequencing revealed a change from AG at codon 135 resulting in a predicted amino acid change of methionine to valine. This same change was also observed in F206 (Mullan et al., *Nature Genet.* 1992, 2:340–343) and segregated with the disease in both families.

Using PCR direct sequencing, families were screened for the presence of further mutations in the five exon fragments. Two different amino acid substitutions at codon 276 and a third substitution at codon 263 were identified.

A CT mutation that results in a ProSer substitution at codon 263 was identified in pedigree F196. This mutation results in a loss of both an AvaII and a Sau961 site.

An AC transversion resulting in an amino acid substitution of glutamic acid to alanine at codon 276 was also identified. This mutation was detected in three kindreds and a single sample available from a fourth family (C1, C2, C3 and 771), all from the province of Atioquia in Columbia. Lopera et al., *Acta Neurologica Columbiana* 1994, 10: 173–187. Individual 771 is from the same region of Columbia and has a positive family history of early onset Alzheimer's disease. The family is thought to be distantly related to the C2 family. Age of onset of the disease is in the late forties. This mutation does not create or destroy restriction enzyme sites. Therefore, a mismatch primer was designed which contained a mismatched base five base pairs from the 3' end of the primer and 6 base pairs away from the mutation. When incorporated into a PCR product, this primer produces a BsmI cut site when the mutation (C) is present. This enables the two alleles to be distinguished by digestion of a PCR product with BsmI. The BsmI recognition sequence is 5'. . . GAATGCN. . . 3' (SEQ ID NO:3) and 3'. . . CTTACGN . . . 5' (SEQ ID NO:4). Primers used in the identification of this mutant are E276:5'-AACAGCTCAGGAGAGGAATG-3' (SEQ ID NO:5); and 952:5'-GATGAGACAAGTNCCNTGAA-3' (SEQ ID NO:6) (Sherrington et al., *Nature* 1995, 375:754–760). DNA (50–100 ng) was used as a template in 25 µl reactions. The reaction mix consisted of 0.2 mM dNTP's, 30 pM each primer, 1×TNK100 buffer, 0.5 U Taq DNA polymerase in final concentration. PCR was carried out under the following conditions: 94° 5 minutes (94° 30 seconds, 45° 30 seconds, 72° 30 seconds)×35 cycles, 72° 3 minutes. BsmI enzyme (5U) was added to the PCR product and digestion was carried out at 65° for 3 hours. The digested product was separated on a 3% agarose gel. A 150 bp fragment of the normal allele and 128+22 bp fragments of the mutated allele are observed. The mutation segregates with the disease. The same base is mutated to G in another family, F183, resulting in a glutamic acid to glycine substitution.

Additional mutations which do not create or destroy any restriction sites, such as a TG polymorphism, can be identified in a similar fashion. A mismatch primer containing two-mismatched base pairs four and five base pairs away from the 3' end of the primer and five and six base pairs from the polymorphism. When incorporated in a PCR product, this primer produces a BamH1 cut site when a G is present and no cut site when a T is present at the polymorphism site. This enables the two alleles to be distinguished by digestion of a PCR product with BamH1. The BamH1 recognition sequence is 5'. . . GGATCC . . . 3' (SEQ ID NO:7) and 3'. . CCTAGG . . . 5' (SEQ ID NO:8). Primers which can be used in the identification of this mutation include: 951 5'-CACCCATTTACAAGTTTAGC-3' (SEQ ID NO:9) (Sherrington et al. Nature 1995, 375:754–760) and T-G BamH1 5'-CACTGATTACTAATTCAGGATC-3' (SEQ ID NO: 10). PCR conditions are similar to those described above. The PCR product is digested by addition of 0.5 U of BamH1 enzyme at 37° C. for 3 hours. The digested products are separated on a 3% agarose gel. A 200 bp fragment of the homozygous normal allele, 182 bp__18 bp fragments of the homozygous mutant allele, and 200 bp+182 bp+18 bp fragments of the heterozygous mutant allele can be observed.

The identification of these mutants provides strong evidence that mutations in the S182 gene are the cause of early onset Alzheimer's disease in Chromosome 14-linked pedigrees. These mutants can be used in the diagnosis of AD and also on the development of models of AD.

At present there is no known effective therapy for the various forms of AD. However, there are several other forms of dementia for which treatments is available and which give rise to progressive intellectual deterioration closely resembling the dementia associated with Alzheimer's disease. A diagnostic test for AD would therefore provide a useful tool in the diagnosis and treatment of these other conditions, by way of being able to exclude early onset Alzheimer's disease. It will also be of value when a suitable therapy for AD does become available.

There are several methodologies available form recombinant DNA technology which may be used for detecting and identifying genetic mutations responsible for Alzheimer's disease. These include, but are not limited to, direct probing, ligase chain reaction (LCR) and polymerase chain reaction (PCR) methodology.

Detection of point mutations using direct probing involves the use of oligonucleotide proves which may be prepared synthetically or by nick translation. In a preferred embodiment, the probes are complementary to at least a portion of the mutant S182 genes, said portion containing the mutation, identified herein. The DNA probes may be suitably labelled using, for example, a radiolabel, enzyme label, fluorescent label, or biotin-avidin label, for subsequent visualization in for example a Southern blot hybridization procedure. The labelled prove is reacted with a sample of DNA from patients suspected of having AD bound to nitrocellulose or Nylon 66 substrate. The areas that carry DNA sequences complementary to the labeled DNA prove become labelled themselves as a consequence of the reannealing reaction. The areas of the filter that exhibit such labeling may then be visualized, for example, by autoradiography.

Alternative probe techniques, such as ligase chain reaction (LCR) involve the use of a mismatch probe, i.e., probes which have full complementary with the target except at the point of the mutation. The target sequence is then allowed to hybridize both with the oligonucleotides having full complementary, i.e., oligonucleotides complementary to the S182 mutants of the present invention, and oligonucleotides containing a mismatch under conditions, it is possible to obtain hybridization only where there is full complementary. If a mismatch is present then there is significantly reduced hybridization.

The polymerase chain reaction (PCR) is a technique that amplifies specific DNA sequences. Repeated cycles of denaturation, primer annealing and extension carried out with a heat stable enzyme Taq polymerase leads to exponential increases in the concentration of desired DNA sequences.

Given the knowledge of nucleotide sequences encoding the S182 gene, it is possible to prepare synthetic oligonucleotides complementary to the sequences which flank the DNA of interest. Each oligonucleotide is complementary to one of the two strands. The DNA is then denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million fold can be achieved. The resulting DNA may then be directly sequenced in order to locate any genetic alterations. Alternatively, the identified S182 mutants of the present invention make it possible to prepare oligonucleotides that will only bind to altered DNA, so that PCR will only result in the multiplication of the DNA if the mutation is present. Following PCR, allele-specific oligonucleotide hybridization may be used to detect the AD point mutation.

Alternatively, an adaptation of PCR called amplification of specific alleles (PASA) can be employed; this method uses differential amplification for rapid and reliable distinction between alleles that differ at a single base pair. Newton et al., *Nucleic Acid Res.* 1989, 17:2503; Nichols et al., *Genomics* 1989, 5:535; Okayama et al., *J. Lab. Clin. Med.* 1989, 1214: 105; Sarkar et al., *Anal. Biochem.* 1990, 186:64; Sommer et al., *Mayo Clin. Proc.* 1989, 64:1361; Wu, *Proc. Nat'l. Acad. Sci. USA* 1989 86:2757; and Dutton et al., *Biotechniques* 1991, 11:700. PASA involves amplification with two oligonucleotide primers such that one is allele specific. The desired allele is efficiently amplified, while the other allele(s) is poorly amplified because it mismatches with a base at or near the 3' end of the allele specific primer. Thus, PASA or the related method PAMSA can be used to specifically amplify one or more variant S182 alleles. Where such amplification is performed on genetic material obtained from a patient, it can serve as a method of detecting the presence of one or more variant S182 alleles in a patient. PCR-induced mutation restriction analysis, often referred to as IMRA, can also be used in the detection of mutants.

Also important is the development of experimental models of Alzheimer's disease. Such models can be used to screen for agents that alter the degenerative course of AD. Having identified specific mutations in the S182 gene as a cause of early onset familial Alzheimer's disease, it is possible using genetic manipulation to develop transgenic model systems and/or whole cell systems containing a mutated S182 gene or a portion thereof. The model systems can be used for screening drugs and evaluating the efficacy of drugs in treating Alzheimer's disease. In addition, these model systems provide a tool for defining the underlying biochemistry of S182 and its relationship to AD thereby providing a basis for rational drug design.

One type of cell system which can be used in the present invention can be naturally derived. For this, blood samples from an affected individual are obtained and permanently transformed into a lymphoblastoid cell line using, for example, Epstein-Barr virus. Once established, such cell lines can be grown continuously in suspension cultures and can be used in a variety of in vitro experiments to study S182 expression and processing. Another cell line used in these studies comprises skin fibroblasts, derived from patients.

Since the FAD mutation is dominant, an alternative method for constructing a cell line is to genetically engineer a S182 mutated gene, or portion thereof, as described herein, into an established cell line of choice. Such methods are well known in the art as exemplified by Sisodia, *Science* 1990, 248:492 and Oltersdork et al., *J Biol. Chem.* 1990, 265:4492, wherein an amyloid precursor peptide gene was transfected into mammalian cells.

Baculovirus expression systems have also been found to be useful for high level expression of heterologous genes in eukaryotic cells.

The mutated gene can also be excised for use in the creation of transgenic animals containing the mutated gene. For example, a mutant S182 gene of the present invention can be cloned and placed in a cloning vector. Examples of cloning vectors which can be used include, but are not limited to, Pcharon35, cosmid, or yeast artificial chromosome. The mutant S182 gene can then be transferred to a host nonhuman animal such as a mouse. As a result of the transfer, the resultant transgenic nonhuman animal will preferably express one or more of the variant S182 polypeptides.

Alternatively, minigenes encoding variant S182 polypeptides can be designed. Such minigenes may contain a cDNA sequence encoding a variant S182 polypeptide, preferably full-length, a combination of S182 exons, or a combination thereof, linked to a downstream polyadenylation signal sequence and an upstream promoter (and preferably enhancer). Such a minigene construct will, when introduced into an appropriate transgenic host, such as a mouse or rat, express a variant S182 polypeptide.

One approach to creating transgenic animals is to target a mutation to the desired gene by homologous recombination in an embryonic stem (ES) cell in vitro followed by microinjection of the modified ES cell line into a host blastocyst and subsequent incubation in a foster mother. Frohman and Martin, *Cell* 1989, 56:145. Alternatively, the technique of microinjection of the mutated gene, or portion thereof, into a one-cell embryo followed by incubation in a foster mother can be used. Additional methods for producing transgenic animals are well known in the art.

Transgenic animals are used in the assessment of new therapeutic compositions and in carcinogenicity testing, as exemplified by U.S. Pat. No. 5,223,610. These animals are also used in the development of predictive animal models for human disease states, as exemplified in U.S. Pat. No. 5,221,778. Transgenic animals have now been developed for assessing Alzheimer's disease (U.S. Pat. No. 7,769,626), multi-drug resistance to anticancer agents (U.S. Pat. No. 7,260,827), and carcinogenic substances (U.S. Pat. No. 4,736,866). Therefore, the mutated genes of the present invention which are believed to cause early onset Alzheimer's disease in Chromosome 14-linked pedigrees provide a useful means for developing transgenic animals to assess this disease.

Site directed mutagenesis and/or gene conversion can also be used to a mutate a non human S182 gene allele, either endogenously or via transfection, such that the mutated gene encodes a S182 polypeptide with an altered amino acid as described in the present invention.

Further, a method has now been developed for the identification of genes exhibiting homology with the S182 gene. For example, a gene homologous to the S182 gene has been identified on chromosome 1. It is believed that this S182-like gene may be the cause of AD in some pedigrees. Using polynucleotide probes made from the polynucleotide sequence set forth in FIG. 1 (SEQ ID NO:24) or using the primers described herein (SEQ ID NO: 1–23), this S182-like gene and others can be identified.

The following nonlimiting examples are provided to further illustrate the present invention.

EXAMPLES

Example 1 cDNA Isolation

A cDNA encoding the entire S182 protein was isolated using the Gene Trapper kit (Gibco BRL, Gaithersburg, Md.) according to manufacturer's instructions. A human Superscript brain library (Gibco BRL) in pCMV.SPORT was probed with the 917 oligonucleotide (Sherrington et al., *Nature* 1995, 375:754–760) which hybridizes to the 5' UTR of the cDNA.

Example 2

PAC Isolation

Inter-Alu PCR was performed on YACs 905C2 and 763B11. Unpurified YAC DNA embedded in agarose was amplified with degenerate primers Alu 5' (5' GGATTACAGG(C/T)(G/A)TGAGCCAC3' (SEQ ID NO: 11) and Alu 3' (5' GAT(C/T)(A/G)(C/T)(G/A)CCA(C/T)TGCACTCC3' (SEQ ID NO: 12). Reactions (100 μl) were heated at 94° C. for 5 minutes and then put through 30 cycles of 94° C. for 1 minute, 55° C. for 1 minute and 72° C. for 2 minutes, with a final extension step at 72° C. for 10 minutes. An aliquot of the amplification products was checked on an agarose gel (1%) and the remainder was purified on Wizard PCR mini-columns (Promega Corp., Madison, Wis.). The inter-Alu probes (100 ng) were labeled to high specific activity with $\alpha$-$^{32}$P dCTP and the Ready-to-Go oligolabelling kit (Pharmacia Biotech Inc., Piscataway, N.J.). Unincorporated nucleotides were removed using a Nick column (Pharmacia Biotech Inc.). Each probe was preblocked for 4 hours with human placental genomic DNA (2 μg/ml final concentration) and then hybridized to high density PAC filters (Genome Systems, Inc.) at 65° C. for 24 hours. Hybridization was in 5×SSC, 1×Denhardt's solution, 0.5% SDS and 100 μg/ml sonicated salmon sperm DNA. The filters were washed to 0.1×SSC/0.1% SDS at 65° C. and then exposed to film for 1–3 days. The filters were probed first with the 905C2 inter-Alu PCR probe, stripped and then rehybridized with the 763B11 probe. All PACs that hybridized to both probes, suggesting a chromosome 14 location, were selected for further analysis.

Example 3

Identification of PAC Terminal Insert Sequences and Exon/Intron Boundaries

The terminal sequences of the human insert of each PAC, and exon/intron boundary sequences were obtained by a ligation-mediated PCR strategy. PAC DNA, purified by a standard plasmid alkaline lysis protocol (Genome Systems, Inc.) was digested with a variety of blunt-cutting restriction enzymes and then ligated to a specially designed linker described by Muelle et al., *Science* 1989, 246:780–786. The terminal insert sequences were then specifically amplified by PCR using a linker-derived primer and either an SP6 sequencing primer (5'-GGCCGTCGACATTTAGGTGACAC (SEQ ID NO: 13)) for PAC end sequencing, or an S182 exon-derived primer for exon/intron boundary sequencing. Sequencing of the products was performed directly in low-melting-point agarose by using a modified dideoxynucleotide sequence method with a $^{32}$P end-labeled primer and Taq DNA polymerase temperature-cycled reactions as described by Srivastava et al., *PCR Methods Appl.* 1992, 1:255–256.

Example 4

Pulsed Field Gel Electrophoresis Sizing of YACs and PACs

The sizes of the CEPH'B' mega YACs were obtained from the CEPH/Genethon database. Cohen et al., *Nature* 1993, 366:696–701. For the St. Louis and CEPH'A'YACs, high molecular weight yeast genomic/YAC DNA was prepared from yeast cells embedded in agarose beads. PAC DNA was prepared by standard plasmid alkaline lysis (Genome Systems, Inc.). Pulsed field gel electrophoresis was performed through 1% agarose in 0.5×TBE buffer (1×TBE=90 mM Tris borate, pH 8.3/2 mM EDTA) at 200 V and 14° C., using Bio-Rad CHEF apparatus. Phage λ concatamers were used as molecular weight standards. The size-fractionated DNAs were depurinated by treatment of the gels with 0.25M HCl for 30 minutes, followed by neutralization in 0.5M NaOH and 1.5M NaCl and alkaline transfer in 0.25M NaOH and 1.5M NaCl onto a nylon membrane (Hybond-N, Amersham Corp., Arlington Hts., Ill.). Hybridizations were carried out in 6×SSC/0.5% SDS/0.1% Ficoll/0.1% bovine serum albumin/0.1% polyvinylpyrrolidone/100 µg/ml sonicated salmon sperm DNA was labeled probe at 65° C. overnight. Washes were performed to a stringency of 0.5× SSC and 0.1% SDS at 65° C.

Example 5

STS Mapping

Oligonucleotide primers for the dinucleotide markers D14S77 and D14S268 were taken from Genethon 1992 and 1994 maps (Weissenbach et al., Nature 1992, 359:794–801; Gynapay et al., Nature Genetics 1994, 7:246–339), and oligonucleotide primers for the ESTs D14S668/D14S677E were taken from GDB, as deposited by Auffray et al., C. R. Acad. des Sciences III 1995, 318:263–272. Oligonucleotide primers were designed for STSs to the YAC/PAC ends, S164 (Sherrington et al., Nature 1995, 375:754–760) and the 5' and 3' UTRs of S182 using the program Oligo 4. To amplify the S164STS, PCR conditions were 30 minutes at 94° C., 30 minutes at 48° C. and 30 minutes at 72° C. for 35 cycles. The S182 5' UTR STS (primers: 5'-AAACGATTTGCGGGGAGAACC (SEQ ID NO: 14) and 5'-TTTGCGATTTTAACAGCATTC (SEQ ID NO: 15)) and 3' UTR STS (primers 5'-CATACTTGTACGCCTCACTTGC (SEQ ID NO: 16) and 5'-ACAGCCATTTTACTCTTCTTT (SEQ ID NO: 17)) were amplified for 30 minutes at 94° C., 30 minutes at 55° C. and 30 minutes at 72° C. for 35 cycles. The STSs 54-12D-R (primers: 5'-TAATATATGCTGGAGGTTTTG (SEQ ID NO: 19)) and 134-8C-R (5'-GATCTGACTAACCAAGTCTTA (SEQ ID NO: 20) and 5'-AGAACTGTAATAGTACTCGAAG (SEQ ID NO: 21)) were amplified for 30 minutes at 94° C., 30 minutes at 50° C. and 30 minutes at 72° C. for 35 cycles.

Example 6

RT-PCR

Poly A+RNA (3 µg) from brain, liver, lung, heart, placenta and skeletal muscle (Clontech Laboratories Inc., Palo Alto, Calif.) was reverse transcribed in six 20 µl reactions with random hexamer primers (100 ng) and Superscript II enzyme (600 units, Gibco BRL) according to manufacturer's instructions. The RNA template was degraded by subsequent treatment with RNAase H (2 units) at 55° C. for 10 minutes. PCR was performed on 1 µl of the unpurified cDNA reaction using primers GP26F (5'-TGCACAGATGTCTGAGGA-3' (SEQ ID NO: 22)) and GP29R (5'-TCCATTAGATAATGGCTCA-3' (SEQ ID NO: 23)). The amplification reaction (25 µl) contained 0.8 µM each primer, 1 mM dNTPs, 1×PCR buffer (Promega Corp.) and 1 unit Taq polymerase (Promega Corp.). The reactions were set up on ice and then heated at 94° C. for 5 minutes, 35 cycles of 94° C. 30 seconds, 46° C. 30 seconds and 72° C. 1 minute were performed before a final extension step at 72° C. for 10 minutes. The amplification products (108 bp and 120 bp) were separated on a 4% Metaphor (FMC Corp. Pine Brook, N.J.) 1% agarose (Promega Corp.) gel and visualized by ethidium bromide staining.

Example 7

PAC Random Genomic Library Construction, Screening And Sequencing

A random shotgun library was prepared from approximately 10 µg of purified recombinant P1-derived artificial chromosome DNA (PAC54-12D). PAC DNA was located from an overnight culture (500 ml of Luria broth supplemented with kanamycin at 20 µg/ml) with an alkaline lysis procedure followed by a solid phase reverse immobilization method using carboxyl coated magnetic particles. The recovered DNA was treated with Plasmid-Safe ATP-Dependent DNase (Epicentre Technologies, Madison, Wis.) at a concentration of 10 units per µg of PAC DNA for 30 minutes at 37° C. to remove any residual bacterial chromosomal DNA contamination. Random DNA fragments were generated by sonication and end-repaired with mung-bean nuclease followed by T4 polymerase and Klenow to remove overhangs and fill-in recesses, respectively. The repaired fragments were size-selected by agarose gel electrophoresis (1–3 kb), recovered and blunt end and ligated to SmaI-cut, phosphatased pUC18 vector. Aliquots of ligated fragments were transformed into Epicurean coli SURE 2 cells (Stratagene, LaJolla, Calif.) and plated directly onto SOB/ampicillin plates. Plasmid templates were prepared from randomly chosen colonies with a 96-well plasmid preparation system (Advanced Genetic Technology Corp., Gaithersburg, Md.). The purified plasmids were gridded and screened by hybridization using radio-labeled S182 cDNA. Sequencing reactions were carried out on the positive recombinant plasmid templates using the Applied Biosystems (AB) Catalyst Lab Station with Applied Biosystems PRISM Ready Reaction Dye Primer Cycle Sequencing Kits for the M13 forward and the M13 reverse primers. Reaction products were run on AB373 DNA Sequencers.

Example 8

Mutation Detection

All families were screened for mutations by PCR followed by restriction digest using the primers described by Sherrington et al., Nature 1995 375:754–760. Restriction digests were electrophoresed on an agarose gel and visualized by ethidium bromide. To determine the precise nature of the mutations that alter restriction digest pattern and to screen for mutations that did not change restriction sites, the same PCRs were performed, but one of the primers was biotinylated. Single stranded DNA template was then derived using streptavidin-coated magnetic beads and a sequencing reaction (Sequenase 2.0 kit, US Biochemical Corp., Cleveland, Ohio) was performed using the DNA still attached to the beads. Automated sequencing of biotinylated PCR products was performed on an ALF sequencer (Pharmacia Biotech Inc.) using the AutoRead and Autoload T7 sequencing kits (Pharmacia Biotech Inc.). Heterozygotes were identified using the ALF manager software package.

Example 9

Detection of E280A Mutation

The A-C mutation at codon 280 of the S182 gene does not create or destroy any restriction enzyme sites. A primer was designed that contains a mismatched base five bases from the 3' end of the primer and 6 bases away from the mutation. When incorporated in a PCR product, this primer produces a BsmI cut site when the mutation (C) is present. This enables the two alleles to be distinguished by digestion of a PCR product with BsmI. DNA 50–100 ng was used as a template in 25µ PCR reactions. The reaction mix consisted of the following final concentrations: 0.2 mM dNTP's, 30 pM each primer (forward primer E276A 5'-AACAGCTCAGGAGAGGAATG-3' (SEQ ID NO:5) and reverse primer 952

5'-GATGAGACAAAGTNCCNTGAA-3' (SEQ ID NO:6), 1×TNK buffer, 0.5 U Taq DNA polymerase. PCR was carried out under the following conditions: 94° C. 5 minutes (94° C. 30 seconds, 45° C. 30 seconds, 72° C. 30 seconds)× 35 cycles, 72° C. 3 minutes. BsmI enzyme (5 U) were added following PCR and digestion carried out at 65° C. for 3 hours. The digested product was electrophoresed on a 3% agarose gel. The normal allele gives a product of 150 bp, whereas the mutant allele gives two products of 128 bp and 22 bp.

What is claimed is:

1. An isolated polynucleotide encoding an S182 protein, wherein said protein consists of the polypeptide of SEQ ID NO:18 and wherein said polypeptide includes a substitution selected from the group consisting of: methionine to valine at amino acid 135, methionine to valine at amino acid 142, proline to serine at amino acid 263, and a glutamic acid to alanine or glycine at amino acid 276.

2. An isolated polypeptide encoded by the polynucleotide of claim 1.

3. The polynucleotide of claim 1 wherein said substitution comprises methionine to valine at amino acid 135, wherein said valine is encoded by nucleotides GTG.

4. The polynucleotide of claim 1 wherein said substitution comprises methionine to valine at amino acid 142, wherein said valine is encoded by nucleotides GTG.

5. The polynucleotide of claim 1 wherein said substitution comprises proline to serine at amino acid 263, wherein said serine is encoded by nucleotides TCA.

6. The polynucleotide of claim 1 wherein said substitution comprises glutamic acid to alanine at amino acid 276, wherein said alanine is encoded by nucleotides GCA.

7. The polynucleotide of claim 1 wherein said substitution comprises glutamic acid to glycine at amino acid 276, wherein said glycine is encoded by nucleotides GGA.

8. A method of detecting a susceptibility to Alzheimer's Disease in a patient comprising:
obtaining a bodily sample from an individual, and detecting a mutation in a polynucleotide of said sample, wherein said polynucleotide encodes an S182 protein, wherein said protein consists of the polypeptide of SEQ ID NO:18 and wherein said polypeptide includes a substitution selected from the group consisting of: methionine to valine at amino acid 135, methionine to valine at amino acid 142, proline to serine at amino acid 263, and a glutamic acid to alanine or glycine at amino acid 276, and wherein said substitution indicates a susceptibility to Alzheimer's Disease.

9. The method of claim 8 wherein said detecting step comprises PCR.

10. The method of claim 8 wherein said substitution comprises methionine to valine at amino acid 135, wherein said valine is encoded by nucleotides GTG.

11. The method of claim 8 wherein said substitution comprises methionine to valine at amino acid 142, wherein said valine is encoded by nucleotides GTG.

12. The method of claim 8 wherein said substitution comprises proline to serine at amino acid 263, wherein said serine is encoded by nucleotides TCA.

13. The method of claim 8 wherein said substitution comprises glutamic acid to alanine at amino acid 276, wherein said alanine is encoded by nucleotides GCA.

14. The method of claim 8 wherein said substitution comprises glutamic acid to glycine at amino acid 276, wherein said glycine is encoded by nucleotides GGA.

15. A method of detecting a susceptibility to Alzheimer's Disease in a patient comprising:
obtaining a bodily sample from an individual, and detecting a mutation in an S182 protein of said sample, wherein said protein consists of the polypeptide of SEQ ID NO:18 and wherein said polypeptide includes a substitution selected from the group consisting of: methionine to valine at amino acid 135, methionine to valine at amino acid 142, proline to serine at amino acid 263, and a glutamic acid to alanine or glycine at amino acid 276, and wherein said substitution indicates a susceptibility to Alzheimer's Disease.

16. The method of claim 15 wherein said substitution comprises methionine to valine at amino acid 135, wherein said valine is encoded by nucleotides GTG.

17. The method of claim 15 wherein said substitution comprises methionine to valine at amino acid 142, wherein said valine is encoded by nucleotides GTG.

18. The method of claim 15 wherein said substitution comprises proline to serine at amino acid 263, wherein said serine is encoded by nucleotides TCA.

19. The method of claim 15 wherein said substitution comprises glutamic acid to alanine at amino acid 276, wherein said alanine is encoded by nucleotides GCA.

20. The method of claim 15 wherein said substitution comprises glutamic acid to glycine at amino acid 276, wherein said glycine is encoded by nucleotides GGA.

21. A method of detecting a mutation in a polynucleotide sequence encoding an S182 protein, wherein said protein consists of the polypeptide of SEQ ID NO:18, comprising:
obtaining a bodily sample comprising said polynucleotide sequence from an individual suspected of having a predisposition to Alzheimer's Disease, and detecting a mutation in said polynucleotide sequence, wherein said mutation consists of a substitution selected from the group consisting of: methionine to valine at amino acid 135, methionine to valine at amino acid 142, proline to serine at amino acid 263, and a glutamic acid to alanine or glycine at amino acid 276.

22. The method of claim 21 wherein said detecting step comprises PCR.

23. The method of claim 21 wherein said substitution comprises methionine to valine at amino acid 135, wherein said valine is encoded by nucleotides GTG.

24. The method of claim 21 wherein said substitution comprises methionine to valine at amino acid 142, wherein said valine is encoded by nucleotides GTG.

25. The method of claim 21 wherein said substitution comprises proline to serine at amino acid 263, wherein said serine is encoded by nucleotides TCA.

26. The method of claim 21 wherein said substitution comprises glutamic acid to alanine at amino acid 276, wherein said alanine is encoded by nucleotides GCA.

27. The method of claim 21 wherein said substitution comprises glutamic acid to glycine at amino acid 276, wherein said glycine is encoded by nucleotides GGA.

28. A method of detecting a mutation in an S182 polypeptide, wherein said polypeptide consists of the polypeptide of SEQ ID NO:18, comprising:
obtaining a bodily sample comprising said polypeptide from an individual suspected of having a predisposition to Alzheimer's Disease, and detecting a mutation in said polypeptide, wherein said mutation consists of a substitution selected from the group consisting of: methionine to valine at amino acid 135, methionine to valine at amino acid 142, proline to serine at amino acid 263, and a glutamic acid to alanine or glycine at amino acid 276.

29. The method of claim 28 wherein said substitution comprises methionine to valine at amino acid 135, wherein said valine is encoded by nucleotides GTG.

30. The method of claim 28 wherein said substitution comprises methionine to valine at amino acid 142, wherein said valine is encoded by nucleotides GTG.

31. The method of claim 28 wherein said substitution comprises proline to serine at amino acid 263, wherein said serine is encoded by nucleotides TCA.

32. The method of claim 28 wherein said substitution comprises glutamic acid to alanine at amino acid 276, wherein said alanine is encoded by nucleotides GCA.

33. The method of claim 28 wherein said substitution comprises glutamic acid to glycine at amino acid 276, wherein said glycine is encoded by nucleotides GGA.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

TCACAGAAGA TACCGAGACT                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

CCCAACCATA AGAAGAACAG                    20

(2) INFORMATION FOR SEQ ID NO:3:

(i) SEQUENCE CHARACTERISTICS:
      (A) LENGTH: 7 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
GAATGCN                                                                    7

(2) INFORMATION FOR SEQ ID NO:4:

(i) SEQUENCE CHARACTERISTICS:
         (A) LENGTH: 7 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

CTTACGN                                                                    7

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

AACAGCTCAG GAGAGGAATG                                                     20

(2) INFORMATION FOR SEQ ID NO:6:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GATGAGACAA GTNCCNTGAA                                                     20

(2) INFORMATION FOR SEQ ID NO:7:

(i) SEQUENCE CHARACTERISTICS:
         (A) LENGTH: 6 base pairs
         (B) TYPE: nucleic acid
         (C) STRANDEDNESS: single
         (D) TOPOLOGY: linear
```

```
        (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

GGATCC                                                                          6

(2) INFORMATION FOR SEQ ID NO:8:

(i) SEQUENCE CHARACTERISTICS:
             (A) LENGTH: 6 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

CCTAGG                                                                          6

(2) INFORMATION FOR SEQ ID NO:9:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

CACCCATTTA CAAGTTTAGC                                                          20

(2) INFORMATION FOR SEQ ID NO:10:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:
```

(xi) SEQUENCE DESCRIPTION: SEQ ID NO:10:

CACTGATTAC TAATTCAGGA TC                                                    22

(2) INFORMATION FOR SEQ ID NO:11:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:11:

GGATTACAGG YRTGAGCCAC                                                       20

(2) INFORMATION FOR SEQ ID NO:12:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:12:

GATYRYRCCA YTGCACTCC                                                        19

(2) INFORMATION FOR SEQ ID NO:13:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:13:

GGCCGTCGAC ATTTAGGTGA CAC                                                   23

(2) INFORMATION FOR SEQ ID NO:14:

(i) SEQUENCE CHARACTERISTICS:
          (A) LENGTH: 21 base pairs
          (B) TYPE: nucleic acid
          (C) STRANDEDNESS: single (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:14:

AAACGATTTG CGGGGAGAAC C                                              21

(2) INFORMATION FOR SEQ ID NO:15:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

TTTGCGATTT TAACAGCATT C                                              21

(2) INFORMATION FOR SEQ ID NO:16:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

CATACTTGTA CGCCTCACTT GC                                             22

(2) INFORMATION FOR SEQ ID NO:17:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

ACAGCCATTT TACTCTTCTT T                                                    21

(2) INFORMATION FOR SEQ ID NO:18:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:18:

```
Met Thr Glu Leu Pro Ala Pro Leu Ser Tyr Phe Gln Asn Ala Gln Met
  1               5                  10                  15

Ser Glu Asp Asn His Leu Ser Asn Thr Asn Asp Asn Arg Glu Arg Gln
             20                  25                  30

Glu His Asn Asp Arg Arg Ser Leu Gly His Pro Glu Pro Leu Ser Asn
         35                  40                  45

Gly Arg Pro Gln Gly Asn Ser Arg Gln Val Val Glu Gln Asp Glu Glu
     50                  55                  60

Glu Asp Glu Glu Leu Thr Leu Lys Tyr Gly Ala Lys His Val Ile Met
 65                  70                  75                  80

Leu Phe Val Pro Val Thr Leu Cys Met Val Val Val Ala Thr Ile
                 85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
             115                 120                 125

Ile Leu Asn Ala Ala Ile Met Ile Ser Val Ile Val Val Met Thr Ile
    130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Phe Glu Ser Phe Ile
                    165                 170                 175

Tyr Leu Gly Glu Val Phe Lys Thr Tyr Asn Val Ala Val Asp Tyr Ile
                180                 185                 190

Thr Val Ala Leu Leu Ile Trp Asn Phe Gly Val Val Gly Met Ile Ser
                195                 200                 205

Ile His Trp Lys Gly Pro Leu Arg Leu Gln Gln Ala Tyr Leu Ile Met
    210                 215                 220

Ile Ser Ala Leu Met Ala Leu Val Phe Ile Lys Tyr Leu Pro Glu Trp
225                 230                 235                 240

Thr Ala Trp Leu Ile Leu Ala Val Ile Ser Val Tyr Asp Leu Val Ala
                    245                 250                 255

Val Leu Cys Pro Lys Gly Pro Leu Arg Met Leu Val Glu Thr Ala Gln
                260                 265                 270

Glu Arg Asp Glu Thr Leu Phe Pro Ala Leu Ile Tyr Ser Ser Thr Met
                275                 280                 285
```

```
Val Trp Leu Val Asn Met Ala Glu Gly Asp Pro Glu Ala Gln Arg Arg
    290                 295                 300

Val Ser Lys Asn Ser Lys Tyr Asn Ala Glu Ser Thr Glu Arg Glu Ser
305                 310                 315                 320

Gln Asp Thr Val Ala Glu Asn Asp Asp Gly Gly Phe Ser Glu Glu Trp
                325                 330                 335

Glu Ala Gln Arg Asp Ser His Leu Gly Pro His Arg Ser Thr Pro Glu
                340                 345                 350

Ser Arg Ala Ala Val Gln Glu Leu Ser Ser Ser Ile Leu Ala Gly Glu
                355                 360                 365

Asp Pro Glu Glu Arg Gly Val Lys Leu Gly Leu Gly Asp Phe Ile Phe
    370                 375                 380

Tyr Ser Val Leu Val Gly Lys Ala Ser Ala Thr Ala Ser Gly Asp Trp
385                 390                 395                 400

Asn Thr Thr Ile Ala Cys Phe Val Ala Ile Leu Ile Gly Leu Cys Leu
                405                 410                 415

Thr Leu Leu Leu Leu Ala Ile Phe Lys Lys Ala Leu Pro Ala Leu Pro
                420                 425                 430

Ile Ser Ile Thr Phe Gly Leu Val Phe Tyr Phe Ala Thr Asp Tyr Leu
                435                 440                 445

Val Gln Pro Phe Met Asp Gln Leu Ala Phe His Gln Phe Tyr Ile
    450                 455                 460
```

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

TAATATATGC TGGAGGTTTT G                                        21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:20:

GATCTGACTA ACCAAGTCTT A                                        21

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

AGAACTGTAA TAGTACTCGA AG                                           22

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

TGCACAGATG TCTGAGGA                                                 18

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

TCCATTAGAT AATGGCTCA                                              19

(2) INFORMATION FOR SEQ ID NO:24:

(i) SEQUENCE CHARACTERISTICS:
        (A) LENGTH: 1914 base pairs
        (B) TYPE: nucleic acid
        (C) STRANDEDNESS: single
        (D) TOPOLOGY: linear (ii) MOLECULE TYPE: cDNA (iii) HYPOTHETICAL: NO -continued (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:24:

```
CCGTACGTAG CCGCGGCGGC AGCGGGGCGG CGGGGAAGCG TATGCATACA AATTTATTAG      60
CATGCAGACT GGGAGAACCA CAAGACCTAA TCTGGGAGCC TGCAAGTGAC AACAGCCTTT     120
GCGGTCCTTA GACAGCTTGG CCTGGAGGAG AACACATGAA AGAAAGAACC TCAAGAGGCT     180
TTGTTTTCTG TGAAACAGTA TTTCTATACA GTTGCTCCAA TGACAGAGTT ACCTGCACCG     240
TTGTCCTACT TCCAGAATGC ACAGATGTCT GAGGACAACC ACCTGAGCAA TACTAATGAC     300
AATAGAGAAC GGCAGGAGCA CAACGACAGA CGGAGCCTTG GCCACCCTGA GCCATTATCT     360
AATGGACGAC CCCAGGGTAA CTCCCGGCAG GTGGTGGAGC AAGATGAGGA AGAAGATGAG     420
GAGCTGACAT TGAAATATGG CGCCAAGCAT GTGATCATGC TCTTTGTCCC TGTGACTCTC     480
TGCATGGTGG TGGTCGTGGC TACCATTAAG TCAGTCAGCT TTTATACCCG GAAGGATGGG     540
CAGCTAATCT ATACCCCATT CACAGAAGAT ACCGACTG TGGGCCAGAG AGCCCTGCAC      600
TCAATTCTGA ATGCTGCCAT CATGATCAGT GTCATTGTTG TCATGACTAT CCTCCTGGTG     660
GTTCTGTATA AATACAGGTG CTATAAGGTC ATCCATGCCT GGCTTATTAT ATCATCTCTA     720
TTGTTGCTGT TCTTTTTTTC ATTCATTTAC TTGGGGGAAG TGTTTAAAAC CTATAACGTT     780
GCTGTGGACT ACATTACTGT TGCACTCCTG ATCTGGAATT TTGGTGTGGT GGGAATGATT     840
TCCATTCACT GGAAAGGTCC ACTTCGACTC CAGCAGGCAT ATCTCATTAT GATTAGTGCC     900
CTCATGGCCC TGGTGTTTAT CAAGTACCTC CCTGAATGGA CTGCGTGGCT CATCTTGGCT     960
GTGATTTCAG TATATGATTT AGTGGCTGTT TTGTGTCCGA AAGGTCCACT TCGTATGCTG    1020
GTTGAAACAG CTCAGGAGAG AGATGAAACG CTTTTTCCAG CTCTCATTTA CTCCTCAACA    1080
ATGGTGTGGT TGGTGAATAT GGCAGAAGGA GACCCGGAAG CTCAAAGGAG AGTATCCAAA    1140
AATTCCAAGT ATAATGCAGA AAGCACAGAA AGGGAGTCAC AAGACACTGT TGCAGAGAAT    1200
GATGATGGCG GGTTCAGTGA GGAATGGGAA GCCCAGAGGG ACAGTCATCT AGGGCCTCAT    1260
CGCTCTACAC CTGAGTCACG AGCTGCTGTC CAGGAACTTT CCAGCAGTAT CCTCGCTGGT    1320
GAAGACCCAG AGGAAAGGGG AGTAAAACTT GGATTGGGAG ATTTCATTTT CTACAGTGTT    1380
CTGGTTGGTA AAGCCTCAGC AACAGCCAGT GGAGACTGGA ACACAACCAT AGCCTGTTTC    1440
GTAGCCATAT TAATTGGTTT GTGCCTTACA TTATTACTCC TTGCCATTTT CAAGAAAGCA    1500
TTGCCAGCTC TTCCAATCTC CATCACCTTT GGGCTTGTTT TCTACTTTGC CACAGATTAT    1560
CTTGTACAGC CTTTTATGGA CCAATTAGCA TTCCATCAAT TTTATATCTA GCATATTTGC    1620
GGTTAGAATC CCATGGATGT TTCTTCTTTG ACTATAACAA AATCTGGGGA GGACAAAGGT    1680
GRTTTTCCTG TGTCCCACAT CTAACAAAGT CAAGATTCCC GKCTGGACTT TTGCAGCTTC    1740
CTKCCAAGTC TTCCTGACCA CCTTGCACTW TTGGACTTTG GARGGAGGTG CCTAKAGAAA    1800
ACGRTTTTGA MCATACTTCA TCGCAGTGGA CTGTGTCCCT CGGTGCAGAA ACTACCAGAT    1860
TTGAGGGACG AGGTCAAGGA GATATGATAG GCCCGGAAGT TGCTGTGCCC ATCA          1914
```